US011471628B1

(12) United States Patent
Lowenstein et al.

(10) Patent No.: US 11,471,628 B1
(45) Date of Patent: *Oct. 18, 2022

(54) SYSTEM AND ASSEMBLY FOR INFLATING AND MONITORING PRESSURE WITHIN A RETAINING CUFF

(71) Applicant: Seedlings Life Science Ventures, LLC, Weston, FL (US)

(72) Inventors: Stephen Jay Lowenstein, Englewood Cliffs, NJ (US); Keith Rubin, Ft. Lauderdale, FL (US); Ken Solovay, Weston, FL (US); Timothy Vandermey, Altamonte Springs, FL (US); Klaus Lessnau, New York, NY (US); Michael R. Cole, Stratham, NH (US)

(73) Assignee: Seedlings Life Science Ventures, LLC, Weston, FL (US)

( * ) Notice: Subject to any disclaimer, the term of this patent is extended or adjusted under 35 U.S.C. 154(b) by 478 days.

This patent is subject to a terminal disclaimer.

(21) Appl. No.: 16/723,257

(22) Filed: Dec. 20, 2019

Related U.S. Application Data

(60) Continuation of application No. 15/170,343, filed on Jun. 1, 2016, now abandoned, which is a division of
(Continued)

(51) Int. Cl.
*A61M 16/04* (2006.01)

(52) U.S. Cl.
CPC ... *A61M 16/044* (2013.01); *A61M 2205/3331* (2013.01); *A61M 2205/505* (2013.01); *A61M 2205/52* (2013.01); *A61M 2205/8212* (2013.01)

(58) Field of Classification Search
CPC ........ A61M 16/044; A61M 2205/3331; A61M 2205/505; A61M 2205/52; A61M 2205/8212
See application file for complete search history.

(56) References Cited

U.S. PATENT DOCUMENTS

| 2,566,806 A | 9/1951 | Miller |
| 3,429,313 A | 2/1969 | Romanelli |

(Continued)

FOREIGN PATENT DOCUMENTS

| CA | 2942726 | 6/2021 |
| JP | 2010148545 | 8/2010 |

(Continued)

OTHER PUBLICATIONS

Carrasquilla, et al., Chemistry a European Journal Communication, Patterned Paper Sensors Printed with Long-Chain DNA Aptamers, 21, 7369-7373, Wiley Online Library, Mar. 27, 2015.

*Primary Examiner* — Victoria Murphy
(74) *Attorney, Agent, or Firm* — Malloy & Malloy, PL

(57) ABSTRACT

A system and accompanying assembly, of integrated or modular construction, for inflating and monitoring pressure within a retaining cuff including a housing having a pressure chamber connected in fluid communication with a fluid pressure source and a fluid communicating connection with the retaining cuff. Associated control circuitry includes a pressure sensor disposable in fluid communication with the pressure chamber and the retaining cuff, via the fluid communicating connection and structured to concurrently determine and monitor pressure within the pressure chamber and the retaining cuff. The control circuitry is cooperatively structured with the pressure sensor and other operative components to establish dynamic multilevel sampling capabilities, calibration parameters stored within the control
(Continued)

circuitry prior to use and limited or single use capabilities of the assembly.

18 Claims, 5 Drawing Sheets

Related U.S. Application Data application No. 14/067,158, filed on Oct. 30, 2013, now Pat. No. 10,493,226.

(60) Provisional application No. 61/788,458, filed on Mar. 15, 2013.

(56) References Cited

U.S. PATENT DOCUMENTS

| | | | |
|---|---|---|---|
| 3,941,149 A | 3/1976 | Mittleman | |
| 4,016,885 A | 4/1977 | Bruner | |
| 4,159,722 A | 7/1979 | Walker | |
| 4,294,251 A | 10/1981 | Greenwald et al. | |
| 4,361,107 A | 11/1982 | Gereg | |
| 4,449,976 A | 5/1984 | Kamen | |
| 4,457,747 A | 7/1984 | Tu | |
| 4,501,273 A | 2/1985 | McGinnis | |
| 4,526,196 A | 7/1985 | Pistillo | |
| 4,583,917 A | 4/1986 | Shah | |
| 4,617,015 A | 10/1986 | Foltz | |
| 4,655,197 A | 4/1987 | Atkinson | |
| 4,663,628 A * | 5/1987 | Duncan | E21B 47/26 700/74 |
| 4,872,483 A * | 10/1989 | Shah | A61M 16/044 137/557 |
| 4,904,238 A | 2/1990 | Williams | |
| 4,924,862 A | 5/1990 | Levinson | |
| 4,998,915 A | 3/1991 | Hannah | |
| 5,009,634 A | 4/1991 | Feldman et al. | |
| 5,218,970 A | 6/1993 | Turnbull et al. | |
| 5,235,973 A | 8/1993 | Levinson | |
| 5,336,183 A | 8/1994 | Greelis et al. | |
| 5,421,325 A | 6/1995 | Cinberg et al. | |
| 5,487,383 A | 1/1996 | Levinson | |
| 5,492,536 A | 2/1996 | Mascia | |
| 5,505,193 A | 4/1996 | Ballini et al. | |
| 5,518,376 A | 5/1996 | Haraoka | |
| 5,542,918 A | 8/1996 | Atkinson | |
| 5,591,130 A | 1/1997 | Denton | |
| 5,637,101 A | 6/1997 | Shillington | |
| 5,649,530 A | 7/1997 | Ballini | |
| 5,902,273 A | 5/1999 | Yang et al. | |
| 5,992,239 A | 11/1999 | Boehringer et al. | |
| 6,018,835 A | 2/2000 | Schonfeld | |
| 6,135,358 A | 10/2000 | Ballini | |
| 6,145,703 A | 11/2000 | Opperman | |
| 6,183,421 B1 | 2/2001 | Bobo | |
| 6,222,456 B1 | 4/2001 | Tice | |
| 6,267,749 B1 | 7/2001 | Miklos et al. | |
| 6,530,898 B1 | 3/2003 | Nimkar et al. | |
| 6,553,993 B2 | 4/2003 | Toti et al. | |
| 6,705,320 B1 | 3/2004 | Anderson | |
| 6,736,792 B1 | 5/2004 | Liu | |
| 6,907,879 B2 | 6/2005 | Drinan et al. | |
| 6,979,316 B1 | 12/2005 | Rubin et al. | |
| 7,018,359 B2 | 3/2006 | Igarashi et al. | |
| 7,063,686 B2 | 6/2006 | Mezzoli | |
| 7,143,763 B2 | 12/2006 | Abate | |
| 7,383,736 B2 | 6/2008 | Esnouf | |
| 7,404,329 B2 | 7/2008 | Quinn et al. | |
| 7,569,031 B2 | 8/2009 | Britto | |
| 7,811,261 B2 | 10/2010 | Rubinstein et al. | |
| 7,959,597 B2 | 6/2011 | Baker et al. | |
| 7,981,077 B2 | 7/2011 | Hoke et al. | |
| 8,033,176 B2 | 10/2011 | Esnouf | |
| 8,048,023 B2 | 11/2011 | Hoke et al. | |
| 8,343,114 B2 | 1/2013 | Mehta | |
| 9,289,547 B2 | 3/2016 | Layer et al. | |
| 10,493,226 B2 | 12/2019 | Lowenstein et al. | |
| 2003/0069549 A1 | 4/2003 | MacMahon et al. | |
| 2003/0089367 A1 | 5/2003 | Abate | |
| 2003/0158527 A1 | 8/2003 | Mezzoli | |
| 2003/0172925 A1 | 9/2003 | Zocca et al. | |
| 2004/0182388 A1 | 9/2004 | Djupesland | |
| 2005/0004498 A1 | 1/2005 | Klupt | |
| 2005/0011282 A1 | 1/2005 | Voege et al. | |
| 2006/0150742 A1 | 7/2006 | Esnouf | |
| 2007/0149922 A1 | 6/2007 | Schneider et al. | |
| 2008/0048879 A1 | 2/2008 | Lipman | |
| 2008/0154183 A1 | 6/2008 | Baker et al. | |
| 2008/0183128 A1 | 7/2008 | Morriss et al. | |
| 2008/0200871 A1 | 8/2008 | Slater et al. | |
| 2008/0221507 A1 | 9/2008 | Hoke et al. | |
| 2008/0264413 A1 * | 10/2008 | Doherty | A61M 16/0051 128/202.27 |
| 2008/0312674 A1 | 12/2008 | Chen et al. | |
| 2009/0120445 A1 | 5/2009 | Chikashige | |
| 2009/0145236 A1 | 6/2009 | Esnouf | |
| 2009/0281483 A1 | 11/2009 | Baker et al. | |
| 2009/0281485 A1 | 11/2009 | Baker et al. | |
| 2010/0016787 A1 | 1/2010 | Shapiro et al. | |
| 2010/0179488 A1 | 7/2010 | Spiegel et al. | |
| 2010/0252048 A1 | 10/2010 | Young et al. | |
| 2010/0312132 A1 | 12/2010 | Wood et al. | |
| 2011/0109458 A1 | 5/2011 | Shipman | |
| 2011/0132369 A1 | 6/2011 | Sanchez | |
| 2011/0144588 A1 | 6/2011 | Taylor et al. | |
| 2011/0220116 A1 | 9/2011 | Lowenstein et al. | |
| 2011/0220118 A1 | 9/2011 | Lowenstein et al. | |
| 2011/0220119 A1 | 9/2011 | Lowenstein et al. | |
| 2012/0179118 A1 | 7/2012 | Hair | |
| 2012/0312300 A1 | 12/2012 | Spiegel et al. | |
| 2013/0012869 A1 | 1/2013 | Cha et al. | |
| 2014/0200507 A1 | 7/2014 | Azeez | |
| 2014/0261443 A1 | 9/2014 | Lowenstein et al. | |
| 2014/0371690 A1 | 12/2014 | Sprada et al. | |

FOREIGN PATENT DOCUMENTS

| | | |
|---|---|---|
| JP | 2016515410 | 5/2016 |
| WO | WO2009119449 | 10/2009 |
| WO | WO2011112231 | 9/2011 |
| WO | WO2011127407 | 10/2011 |

* cited by examiner

SYSTEM AND ASSEMBLY FOR INFLATING AND MONITORING PRESSURE WITHIN A RETAINING CUFF

CLAIM OF PRIORITY

The present application is a continuation application to previously filed application having Ser. No. 15/170,343, filed on Jun. 1, 2016, which was a divisional application of previously filed application having Ser. No. 14/067,158, filed on Oct. 30, 2013, which claims priority to a provisional patent application having Ser. No. 61/788,458 and a filing date of Mar. 15, 2013, and which all incorporated herein by reference.

BACKGROUND OF THE INVENTION

Field of the Invention

This invention relates to a system and related assembly for inflating and electronically monitoring pressure within a retaining or pressure cuff such as, but not limited to, the type used to effectively maintain the position of an endotracheal tube within the trachea. In addition to the inflating structure of the assembly, control circuitry is cooperatively structured with other operative components of the assembly to include multilevel sampling capabilities dependent, at least in part, on a time basis and a pressure stability within the retaining cuff. The assembly may also be structured for single or limited use monitoring sessions and preferably includes a self-contained power source.

DESCRIPTION OF THE RELATED ART

The use of endotracheal tubes is well known in the medical profession. In practice, the tube is inserted through the mouth, nose or tracheotomy of the patient into the trachea and is structured, when properly positioned, to facilitate ventilation from a ventilator or the like.

As conventionally used, the endotracheal tube and/or tracheostomy tube includes a coupling structure at the proximal or outer end thereof which connects the lumen of the endotracheal and/or tracheostomy tube to the source of ventilation. The endotracheal and/or tracheostomy tube commonly includes an inflatable, pressure or retaining cuff which is generally disposed in surrounding relation to the distal end of the tube. In use, the cuff is inflated and thereby serves to secure or stabilize the position of the tube as it expands radially outward into confronting relation to the walls of the trachea. As a result, the inflated cuff serves to stabilize the position of the endotracheal tube and also establishes a seal within the trachea. As conventionally structured, a conduit is associated with the endotracheal tube and includes an interior lumen used to inflate the cuff when the endotracheal tube is properly positioned within the trachea. Dependent on the structure and use of the endotracheal tube, the inflating line or conduit may be integrally formed on or within the primary wall of the tube itself. As such, the cuff is manually inflated by an appropriate inflation assembly such as, but not limited to, a separate, removable syringe connected in fluid communication with the outlet lumen. Moreover, the cuff is inflated to a pressure which accomplishes the above noted seal with the interior of the trachea, as well as effect the aforementioned stabilization of the endotracheal and/or tracheostomy tube.

The importance of under inflation, over inflation and/or excessive pressurization of the retaining cuff is well recognized, due to the potential of resulting injury and/or trauma to the patient. Accordingly, when the pressure within the cuff is too low, the sealing function thereof cannot be fully achieved resulting in possible leakage of saliva, air, etc. into the trachea. However, an over pressurization of the cuff may result in reduced blood flow to tracheal tissue, tracheal ischemic conditions, and cause ulcers, bleeding and tracheal stenosis or tracheomalacia after removal of the tube, which can lead to the need for tracheal repair surgery or even a tracheal transplant. Accordingly, it is important to maintain the inner pressure of the cuff, depended on its structure and design, within predetermined ranges in order to affect both the above noted fluid seal with the trachea as well as stabilization of the endotracheal tube within the trachea.

Known attempts to overcome problems of the type set forth above have resulted in the provision of various types of pressure gauges or other pressure monitoring devices connected in fluid communication with the outlet lumen and with the pressure or retaining cuff itself. However, many of these known or conventional attempts to accurately monitor cuff pressure have resulted in less than accurate or satisfactory results. Accordingly, while known monitoring devices may be at least minimally effective for their intended function, they have been found to be relatively bulky, cumbersome, costly, and/or less than efficient. Indeed, because of these factors, monitoring devices are often not available at the bed side and ET cuff pressure monitoring is often inadequately addressed, both initially as well as after the patient is intubated.

Moreover, even if a one time, initial pressure identification is achieved, such is inadequate because the pressure can change over time, such as when the patient is moved or the endotracheal tube is repositioned, or when ventilation settings are adjusted. As a result, there is a need in the medical profession for an assembly structured to properly inflate and adequately monitor the pressure within a retaining or pressure cuff of an endotracheal and/or tracheostomy tube. Further, the inflating and monitoring functions of a proposed monitoring assembly should preferably be carried out by a single unit which may be incorporated within the endotracheal tube assembly or alternatively may be connected thereto. As such, the monitoring of the pressure within the retaining cuff should be effectively accomplished by a mere visual observation of the preferred assembly, without requiring repeated attachment and removal of a pressure monitor and/or inflating device. In addition, such a preferred monitoring and inflating assembly should be easily operable, and in certain preferred embodiments may be structured to be used as a single use device, which is not integrated into the endotracheal tube, but readily connectable to an inflation lumen of the tube and subsequently detachable there from, but further wherein reconnection of the monitoring assembly is prevented so that reuse of the device is prevented to avoid cross-contamination of infection from patient to patient.

Further, in addition to its applicability within the pressure or retaining cuff associated with an endotracheal tube, it is also recognized that such a structure would be highly beneficial for use within a variety of different medical devices, including the pressure or retaining cuffs, often referred to as balloons or bladders, used in balloon kyphoplasty, balloon sinuplasty, coronary or vascular balloon angioplasty and/or the delivery of stents, balloon esophageal dilation, and the dilation of strictures and sphincters, balloon dilatation of the nephrostomytract, and/or Swan Ganz catheters, among other medical devices.

SUMMARY OF THE INVENTION

The present invention is directed to a system and an attendant assembly for inflating a retaining cuff to an intended and/or predetermined pressure and monitoring the pressure thereof, once inflated. As used herein, the term "retaining cuff" is meant to primarily include a pressure or retaining cuff for an endotracheal tube. However, the system and assembly of the present invention may be used with a variety of pressure or retaining cuffs structured for use in different medical procedures or instrumentation.

In more specific terms, the system and assembly of the present invention includes a housing having an interior pressure chamber and an inlet and an outlet disposed in direct fluid communication with the pressure chamber. The inlet is structured for connection to a fluid pressure source such as, but not limited to, a syringe-like structure including a plunger and a delivery nozzle or portion which may comprise a male lure connector. When so structured, the male lure connector should be dimensioned and configured to be inserted in the inlet of the pressure chamber. The outlet of the pressure chamber is structured for connection with a fluid communicating connection with the retaining cuff by virtue of a conduit, outlet lumen, pilot balloon, etc., connected to the retaining cuff.

Control circuitry is connected to or defines at least a part of the housing and includes a micro processor, a pressure sensor, as well as other operative components associated with the intended features of the monitoring function of the present invention. The pressure sensor is preferably in the form of a sensor module and the pressure sensor or sensor module is disposed in fluid communication with the pressure chamber. As such, the sensor module and the cooperative components of the control circuitry are cooperatively structured to determine and monitor pressure within the pressure chamber. Further, due to the aforementioned fluid communicating connection between the pressure chamber and the retaining cuff, the pressure within the pressure chamber is substantially the same as that within the retaining cuff. As a result, the determination and/or monitoring, by the sensor module, of the pressure within the pressure chamber will result in a determination, monitoring and indication of the same pressure within the retaining cuff.

Yet additional structural and operational features of the system and assembly of the present invention include the control circuitry comprising sufficient memory or memory capabilities to facilitate it storing calibration values or "calibration parameters". More specifically, the assembly of the present invention is self-calibrating and the corresponding calibration values will be stored in the non-volatile memory and then be placed in a "no-power state". Accordingly, the assembly is shipped from the factory with no power applied to the control circuitry. The control circuitry remains in this "no-powered" mode until the monitoring assembly of the present invention is first activated. Upon a first or initial activation electrical energy, such as from a self-contained power source, is directed to the control circuitry, microprocessor, etc. to facilitate the first or initial activation. Immediately subsequent to the initial or first activation and from that point on, the control circuitry or more specifically the microprocessor, pressure sensor or sensor module and possibly other operative components associated therewith, will be either in a "sleep mode" or "sensor power mode".

In addition, when in the sleep mode certain "low power" components operatively associated with control circuitry including, but not limited to the display device may draw relatively small amounts of current until fully activated. However, the pressure sensor or sensor module draws a relatively greater amount of current and as such will be maintained in a "power-off" mode when not activated, such as when the pressure is not being monitored. As a result of the above, the operable life of the self-contained power source or battery is extended.

The aforementioned calibration parameters will be directly associated with and/or at least partially dependent on intended utilization of the system and assembly; the length of an intended monitoring session; cooperative structuring and operation of the various components and/or other operative features of the system and assembly. However, all of the aforementioned calibration parameters or values needed for the accurate determination and display of pressure readings and/or determination and maintenance of pressure values of the retaining cuff and pressure chamber, will be stored prior to a first use or first activation of the assembly. More specifically, when the assembly is being structured, assembled and/or programmed for use and prior to its initial use or activation, all of the calibration parameters and data are stored into the non-volatile memory of the control circuitry.

Further, the memory is structured to store and/or maintain the calibration parameters, wherein the control circuitry is then placed in the aforementioned in the "no-powered mode", as set forth during shipment and prior to its first or initial activation. Moreover, upon an initial or first activation when the assembly is ready for use, the calibration parameters relating to the intended monitoring capabilities of the monitoring assembly will be implemented. Accordingly, there is no need to calibrate the control circuitry and/or other operative components of the assembly after it has been initially activated for its first use in a monitoring session.

The housing of the inflating and monitoring assembly may also include the aforementioned display device preferably, but not necessarily, in the form of a display screen having "touch activation" features operative to selectively activate and control operation of the display device and in certain embodiments activation of other components of the monitoring assembly. In use, the display device will provide a visual indication of the pressure values or pressure readings of the retaining cuff. As further noted, the display device is operative on a very "low power" basis and as such may draw a small amount of current when it and the microprocessor, associated with the control circuitry, are in the "sleep mode" after a first or initial activation of the monitoring assembly. It is again emphasized that before the initial or first activation or use of the monitoring assembly, the operative components, including the control circuitry, are in the aforementioned "no-powered mode", in that no power is applied to the control circuitry during assembly or shipping.

In at least one embodiment, cooperative structuring between the display device and control circuitry facilitates the powering-up of the microprocessor upon a selective activation of the display device, such as by utilizing the aforementioned touch activation of the display device. In contrast, even when not performing a monitoring, reading or display of a pressure value of the retaining cuff, the display device will normally remain in an active state even when the microprocessor and the pressure sensor or sensor module are in the sleep mode. This is due in part to the fact that the display device operates on extremely low power. Accordingly, the difference between the "sleep mode" and the "sensor power mode" is that the pressure sensor and the microprocessor are running and active during the "sensor power mode". In contrast, when in the "sleep mode" the pressure sensor or sensor module and the microprocessor are virtually powered off, at least to the extent that only a few exceptionally low power functions are operable.

Other operative features associated with one or more preferred embodiments of the present invention are also directly associated with the conservation of power in order to extend the operable life of the self-contained power source. Accordingly, the control circuitry and microprocessor are operatively structured with the sensor module to include "multilevel sampling capabilities" which is effective to accomplish power modulation to the pressure sensor or sensor module. More specifically, the multilevel sampling capabilities comprise a sampling or monitoring of the pressure of the retaining cuff at different rates or frequencies. Therefore, the multilevel sampling capabilities include at least a high rate sampling mode and a low rate sampling mode. Further, the high rate sampling mode includes a sampling frequency sufficient to determine substantially real-time pressure values of the retaining cuff and may occur at multiple times per second such as, but not limited to, 4 times per second. In contrast, the low rate sampling mode comprises a sampling frequency of generally about once every 1-2 seconds. Therefore, power to and consumed by the pressure sensor or sensor module varies, so as to conserve energy of the self-contained power source or battery associated with the monitoring assembly. As such, during the high rate sampling mode, the pressure sensor will maintained in the "sensor power mode" a sufficient amount of time to obtain pressure readings at the higher sampling rate. Therefore, more power will be consumed by the pressure sensor during this high rate sampling mode. In contrast, the pressure sensor will be allowed to assume the "sleep mode" and thereby consume less energy during the low rate sampling mode. This is due, as set forth above, to the fact that the sensor module may be activated only about once every 1-2 seconds, rather than multiple times per second as is the case during the high rate sampling mode. It is therefore again emphasized that the variation in sampling rates, as well as the overall capability of placing the microprocessor and the pressure sensor in either the "sleep mode" or "sensor power mode" serves to effectively save energy delivered by the self-contained power source.

In addition, the multilevel sampling capabilities include dynamic operating characteristics comprising automatic changes of sampling rates or frequencies, dependent at least in part on a "time basis" as well as the pressure stability of the retaining cuff. Accordingly, when the pressure within the retaining cuff remains substantially stable over a period of time, for example two minutes, the dynamic operating characteristics of the multilevel sampling capabilities will automatically change the frequency of sampling from the high rate sampling mode to the low rate sampling mode. In addition, the sampling rate or sampling frequency will automatically be changed back from the low rate sampling mode to the high rate sampling mode upon the determination of an actual change in the pressure or retaining cuff or the occurrence of one or more predetermined external events.

As also described in greater detail hereinafter, the occurrence of a predetermined external event may also cause the dynamic operating characteristics to automatically change the sampling rate or frequency from the low rate sampling mode to the high rate sampling mode when any event occurs which would appear to affect the pressure within the retaining cuff. By way of example only, a manual adjustment or inadvertent manipulation of the fluid communicating connection of the retaining cuff with the outlet of the pressure chamber may be interpreted by the control circuitry as an attempt to remove the retaining cuff from its intended fluid communication with the pressure chamber. In order to assure a real-time evaluation of the pressure within the retaining cuff during an external event, the high rate sampling mode will be established in order to accurately determine the pressure of the retaining cuff. However, the external event such as, purposefully or inadvertently, manipulating the fluid communicating connection may in fact not result in a reduction of the pressure within the retaining cuff.

Yet additional features of one or more preferred embodiments of the system and assembly include "limited use capabilities" comprising structuring the control circuitry for permanent deactivation after use. Moreover, the limited use capabilities may comprise operative features which allow the assembly to be a single use device or alternatively capable of being used for a limited or predetermined number of monitoring sessions. In accordance therewith, a switching assembly may be connected to the housing and directly associated with the outlet of the pressure chamber. When so disposed or otherwise operatively positioned, the switching assembly is structured to deactivate the control circuitry upon the removal of the aforementioned fluid communicating connection from the outlet. The switching assembly may also be structured to activate the control circuitry upon the introduction or establishment of the fluid communicating connection with the outlet. This initial activation may occur when the retaining cuff is initially connected in fluid communication with the interior of the pressure chamber by virtue of the outlet. As set forth above, the control circuitry may normally or initially be disposed in a sleep mode and will not be activated. However additional structural and operative features associated with the switching assembly may include an automatic activation of the control circuitry upon establishment of the fluid communicating connection of the retaining cuff with the outlet.

As set forth above, one or more embodiments of the assembly may include the aforementioned limited use capabilities. As a result the removal of the fluid communicating connection of the retaining cuff with the pressure chamber, through the outlet, may in turn result in the assembly being incapable of being used after such removal. However, in order to overcome any inadvertent manipulation, handling or external event which would be perceived by the control circuitry as an attempt to disconnect the fluid communicating connection, the control circuitry includes a "time delay facility". The time delay facility is operatively connected to the control circuitry. The time delay facility is structured to delay deactivation of the control circuitry for a predetermined time period upon an at least partially disconnection of the fluid communicating connection. Therefore, any inadvertent contact or manipulation with the fluid communicating connection which would be interpreted by the control circuitry as an attempt to disconnect the fluid communicating connection will not, at least for a period of time, result in the prevention of utilizing the repeated use of the monitoring assembly. Such predetermined time period associated with the time delay facility may be as little as a few seconds or as long as one or more minutes, before the remainder of the monitoring assembly is rendered inoperable and incapable of a repeated use. This time delay will allow a user to reconnect the fluid communicating connection or make other adjustments which will prevent the control circuitry from becoming inoperable.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
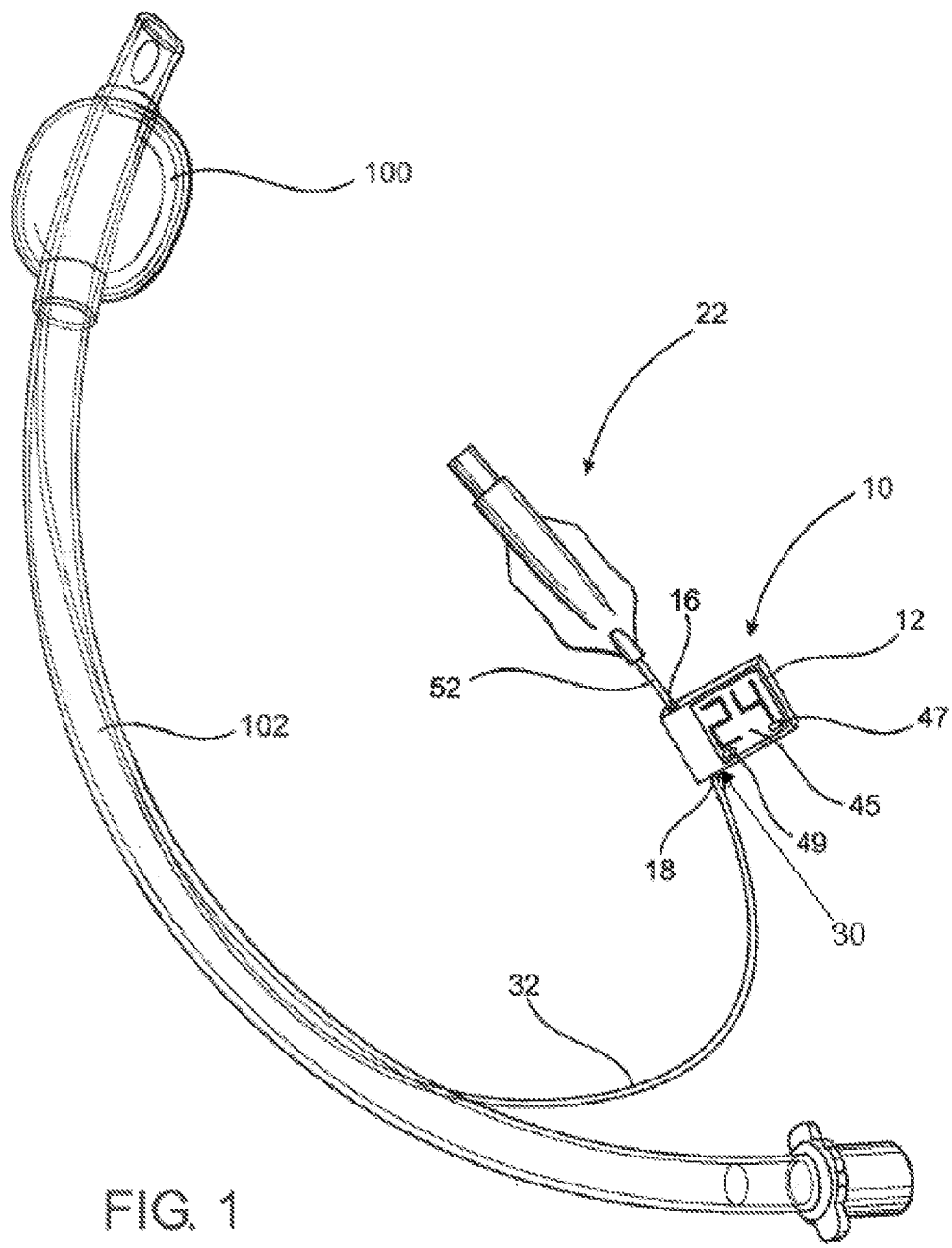
FIG. 1 is a perspective view of a monitoring assembly of the present invention operatively integrated or modularly connected with a pressure cuff of the type associated with an endotracheal tube as well as a fluid pressure source.
Figure 2:
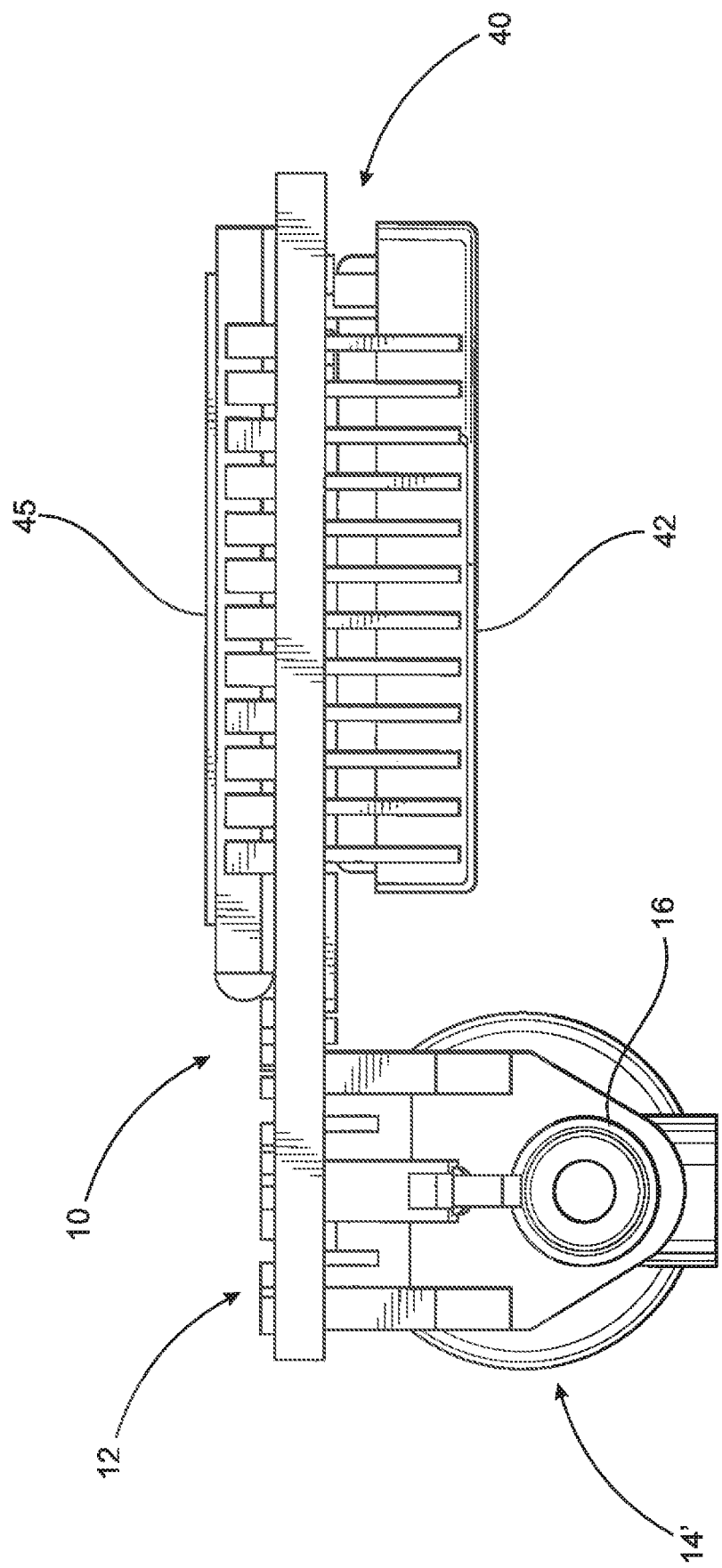
FIG. 2 is an end perspective view of the inflating and pressure monitoring assembly of the system of the present invention.
Figure 3:
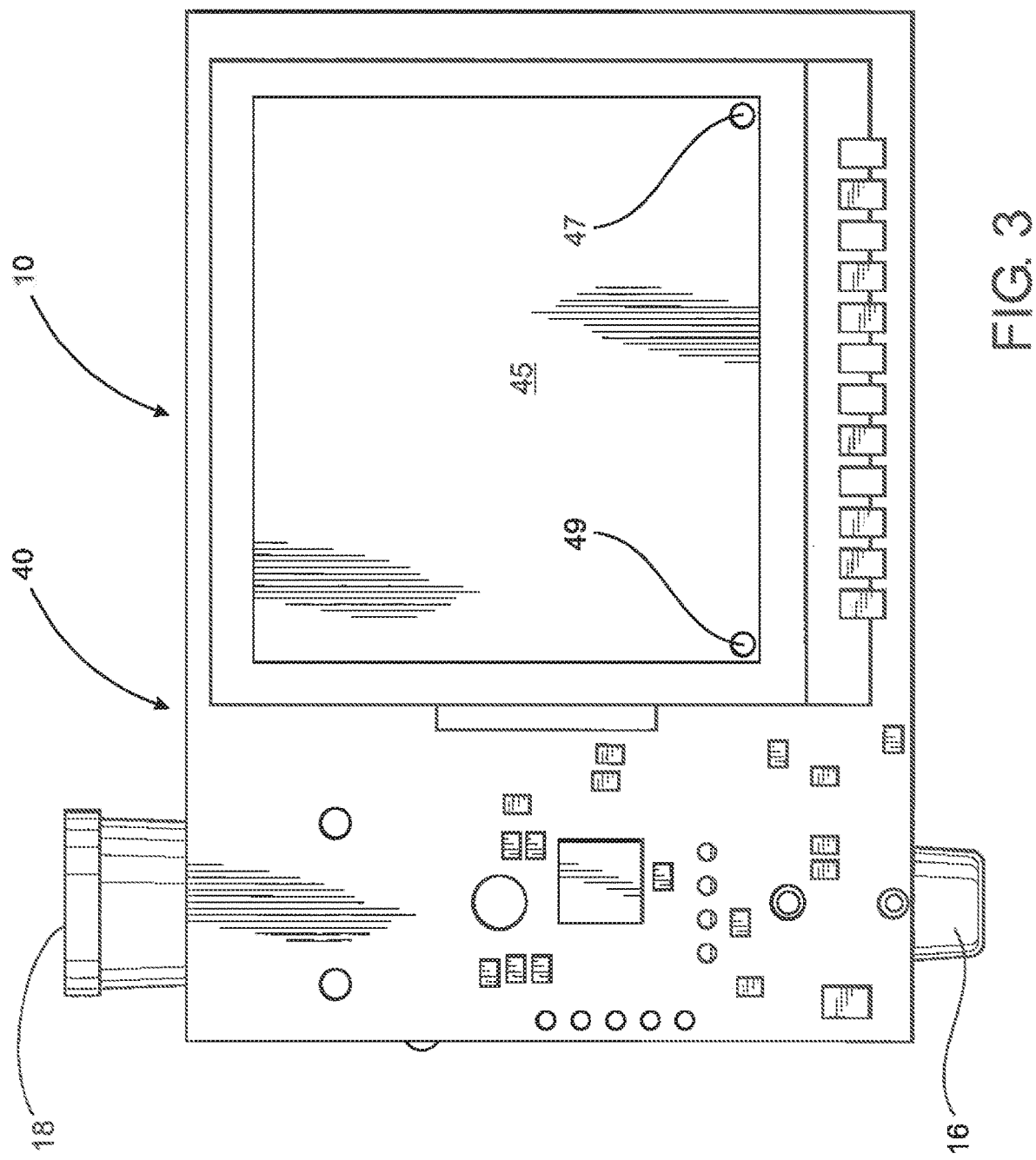
FIG. 3 is a top view of FIG. 2 representing a display structure associated a housing and control circuitry of the present invention.

The present invention is directed to a system and accompanying assembly, generally indicated as 10, for inflating and monitoring pressure within a pressure or retaining cuff 100 such as, but not limited to the type that maintains proper position of an endotracheal tube 102 within the trachea of the patient. For purposes of clarity descriptive legends are present in the schematic, perspective view of FIG. 1. Also, the operative features and components of the inflating and monitoring assembly 10 of the present invention are further represented by appropriate reference numerals in FIGS. 2 through 5.

More specifically, the assembly 10 includes a casing or housing, generally indicated as 12, including a pressure chamber 14 (see FIG. 5), which may be disposed within the interior of a chamber housing 14'. The pressure chamber 14 and chamber housing' 14' include an inlet generally indicated as 16 and an outlet generally indicated as 18 both disposed in fluid communication with the pressure chamber 14, 14'. In at least one preferred embodiment, the inlet 16 is in the form of a female luer-type connector dimensioned and configured to removably receive a dispensing portion 20 of a fluid pressure source 22 therein. As also schematically represented in FIGS. 2 through 5, the source of fluid pressure 22 may be in the form of a syringe-like structure having a plunger disposed within the interior of a barrel or hollow body portion 23. When manipulated, the syringe-type structure 22 serves to direct fluid under pressure through the nozzle or dispensing portion 20 into the interior of the pressure chamber 14. Cooperative structuring between the dispensing portion 20 and the inlet 16 will facilitate the initial displacement of a valve member 26 which is normally disposed in sealing relation to the inlet 16.

Figure 4:
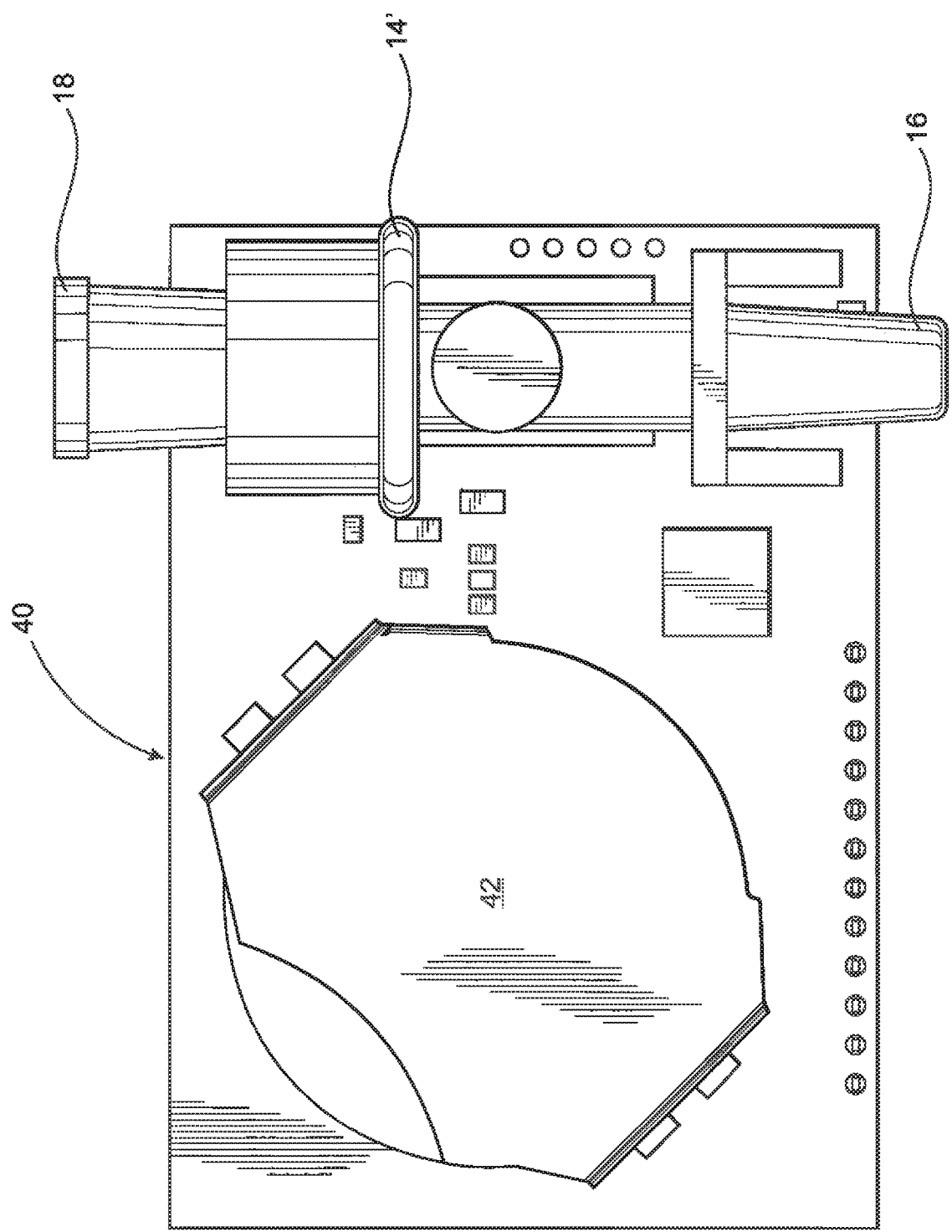
FIG. 4 is a bottom view of the embodiment of FIG. 2 representing a power source associated with control circuitry for powering the various operative components of the system of the present invention.

In more specific terms, insertion of the dispensing portion 20 will move the valve 26 into a position where and associated seal member 28 is disposed out of sealing engagement with interior portions of the chamber 14. As a result, fluid under pressure will flow into the pressure chamber 14 and eventually out of the outlet 18. With reference to FIG. 4, the outlet 18 is disposed, dimensioned and configured to establish a fluid communicating connection, generally indicated as 30, with an outlet lumen, pilot balloon, fluid connecting conduit, etc. which is disposed in direct fluid communicating relation with the retaining or pressure cuff 100, as represented in FIG. 1. Moreover, the fluid outlet lumen 32 may be in the form of a female male luer-type connector dimensioned and configured for mating, fluid transferring or conducting engagement with the outlet 18, in the form of a male luer-type connector, so as to at least partially define the fluid communicating connection 30, as represented. It should be further noted that upon removal of the fluid pressure source 22 and withdrawal of the dispensing portion 20, the valve 26 will normally assume its sealed orientation, wherein seal 28 is disposed in its sealing orientation. As indicated and represented at least in FIG. 4, the sealing orientation thereby prevents the escape of pressure within the pressure chamber 14 through the inlet 16. Also, it is emphasized that when the fluid pressure source 22 is operated, fluid will flow, under pressure, into the pressure chamber 14 and be transferred through the fluid communicating connection 30 and outlet lumen or like structure 32 to inflate and pressurize the retaining cuff 100. As a result, the pressure within the pressure chamber 14 will be the same as that within the pressure or retaining cuff 100.

In addition to the inflating structure and associated components, as generally set forth above, the inflating and monitoring assembly 10 of the present invention includes cooperatively structured and operative components which facilitate the electronic monitoring of the pressure within the pressure or retaining cuff 100. As such, the housing 12 has appropriate control circuitry, generally indicated as 40, connected thereto or mounted thereon. The control circuitry 40 preferably includes an ultra-low power microcontroller as well as additional electronic components further defining the control circuitry 40. In addition, the control circuitry 40 as well as other electronically powered features of the monitoring and inflating assembly 10, include the provision of a high-energy density, single use, single cell battery generally indicated as 42. Moreover, as will be explained in greater detail hereinafter, the self-contained power source or battery 42 will be appropriately structured to power the microprocessor and other electronic components of the control circuitry 40, a pressure sensor or pressure module 44 as well as a display device 45 for intended operation through at least one "monitoring session". As is recognized in the medical profession, a typical or conventional session associated with the use of the endotracheal tube 102 is generally about two weeks. Therefore the self-contained power source or battery 42 will be structured to last through such a conventional time required to complete at least one monitoring session of at least generally about 2 weeks.

The assembly of the present invention is self-calibrating and the corresponding calibration values or calibration parameters will be stored in a non-volatile memory of the circuitry 40. The control circuitry 40 will then be placed in a "no-power state". Accordingly, the assembly is shipped from the factory with no power applied to the control circuitry 40. The control circuitry 40 remains in this "no-powered" mode until the monitoring assembly 10 of the present invention is first activated. More specifically, the monitoring assembly 10 of the present invention is shipped from the factory, subsequent to manufacture and assembly, with no power applied to the control circuitry 40. The control circuitry 40 remains in this "no-powered" mode until the monitoring assembly 10 is first activated. Upon a first or initial activation electrical energy, such as from the self-contained power source 42, is directed to the control circuitry and microprocessor 40, etc. to facilitate the first or initial activation of the monitoring assembly 10. Immediately subsequent to the initial or first activation and from that point on, the control circuitry 40 or more specifically the microprocessor, pressure sensor or sensor module 44 and possibly other operative components associated therewith, will be either in a "sleep mode" or "sensor power mode".

The aforementioned calibration parameters or values will be directly associated with and/or at least partially dependent on intended utilization of the system and monitoring assembly 10; the length of an intended monitoring session; cooperative structuring and operation of the various components and/or other operative features of the system and monitoring assembly 10. However, all of the aforementioned calibration parameters needed for the accurate determination and display of pressure readings and/or determination and maintenance of pressure values of the retaining cuff 100 and pressure chamber 14, will be downloaded prior to a first use or first activation of the assembly. More specifically, when the assembly is being structured, assembled and/or programmed for use and prior to its initial use or activation, all of the calibration parameters and data are downloaded into the memory of the control circuitry.

Further, the memory is structured to store and/or maintain the downloaded calibration parameters while the control circuitry 40 is in the "no-powered mode", as set forth above, prior to its first or initial activation. Moreover, upon an initial or first activation when the monitoring assembly 10 is ready for use, the aforementioned calibration parameters relating to the intended monitoring capabilities of the monitoring assembly 10 will be implemented. Accordingly, there is no need to calibrate the control circuitry 40 and/or other operative components of the assembly after it has been initially activated for its first use in a monitoring session.

As set forth above, after the initial or first activation, the control circuitry and microprocessor 40, pressure sensor or sensor module 44 and possibly other operative components associated therewith, will be either in a "sleep mode" or "sensor power mode". As also set forth herein, the various operative components of the monitoring assembly 10 are powered by the self-contained battery source 42. It is also noted that the power requirements of the pressure sensor 44 is significantly greater, in orders of magnitude higher, than other components operatively associated with the control circuitry 40. In order to save battery life and reduce power output, the power to the pressure sensor 44 may be modulated or supplied on a periodic basis rather than continuously. As a result, the pressure sensor 44 and the microprocessor associated with the control circuitry 40 may be disposed in either the aforementioned "sleep mode" or the "sensor power mode" after the initial activation or use of the monitoring assembly 10.

In addition, when in the sleep mode certain "low power" components operatively associated with control circuitry 40 including, but not limited to the display device 45, may draw relatively small amounts of current until fully activated. However, as indicated, the pressure sensor or sensor module 44 draws a relatively greater amount of current and as such will be maintained in the "sleep mode" when not activated, such as when the pressure is not being monitored. As a result of the above, the operable life of the self-contained power source or battery 42 is extended. Also, in at least one embodiment, cooperative structuring between the display device 45 and control circuitry 40 facilitates the powering-up of the microprocessor control circuitry 40 upon a selective activation of the display device, such as by utilizing the aforementioned touch activation of the display device. In contrast, even when not performing a monitoring, reading or display of a pressure value of the retaining cuff 100, the display device 45 will normally remain in an active state even when the microprocessor of the control circuitry 40 and the pressure sensor or sensor module 44 are in the sleep mode. This is due in part to the fact that the display device 45 operates on extremely low power.

Accordingly, the difference between the "sleep mode" and the "sensor power mode" is that the pressure sensor 44 and the microprocessor 40 are running and active during the "sensor power mode". In contrast, when in the "sleep mode" the pressure sensor or sensor module 44 and the microprocessor 40 are virtually powered off, at least to the extent that only a few exceptionally low power functions are operable.

Figure 5:
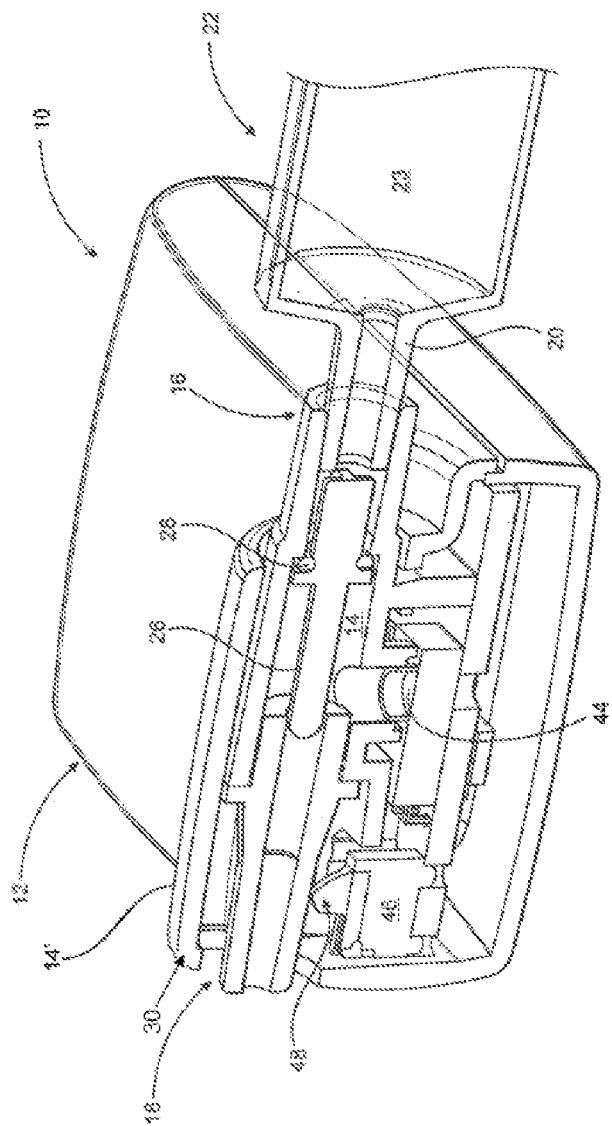
FIG. 5 is a perspective view in section representing interior portions of one embodiment of the housing and operative components of the embodiment of FIGS. 1-3.

With primary reference to FIG. 5, additional features of the inflating and monitoring assembly 10 include provision of the pressure sensor in the form of a sensor module 44 operatively associated with the control circuitry and microprocessor 40. As represented, the pressure sensor or sensor module 44 is disposed in direct fluid communication with the pressure chamber 14 on the interior of the pressure chamber housing 14'. As such, once the retaining or pressure cuff 100 has been inflated and pressurized, as set forth above, the pressure within the pressure chamber 14 will be substantially the same as that maintained within the retaining cuff 100. Therefore, the exposure and/or fluid communication of the sensor module 44 to the interior pressure chamber 14 will result in the sensor module 44 determining or "sensing" the common pressure existing within the pressure chamber 14 and the retaining cuff 100. As a result, the control circuitry and microprocessor 40, through the operative capabilities of the sensor module 44, will provide an accurate and reliable electronic monitoring of the pressure within the retaining cuff 100 on a real-time or other predetermined basis, as explained in greater detail hereinafter.

Yet additional structural and operative features of one or more preferred embodiments of the inflating and monitoring assembly 10 include the provision of a switching assembly 46. The switching assembly 46 is mounted on or connected to the body 12 and includes at least one switch member 48. The switch member 48 is preferably, but not exclusively, disposed in direct, operative association with the outlet 18. As a result, the insertion of an outlet lumen 32 within the outlet 18 will establish a fluid communicating connection with an outlet lumen 32. Such insertion or connection results in the interaction, engagement or "tripping" of the switching member 48 and switching assembly 46 by the outlet lumen 32, in the form of a female luer-type connector into the male luer-type connector of the outlet 18. In addition, the switching assembly 46 is operatively connected to the microprocessor and control circuitry 40. As such, cooperative structuring between the switching assembly 46 and a remainder of the control circuitry 40 results in the activation and/or deactivation of the control circuitry 40, specifically including, but not limited to, the initial or first activation of the monitoring assembly 10. This is dependent on an insertion or removal of the outlet lumen 32 relative to the outlet 18, at least to the extent of connecting or disconnecting the fluid communicating connection 30, as explained in greater detail herein.

Yet additional features of the inflating and monitoring assembly 10 of the present invention include the aforementioned display device 45. In at least one preferred embodiment, the display device 45 may include a display screen having "touch activation" capabilities. Further, the display device 45 is operatively connected to remaining portions of the microprocessor and control circuitry 40 and as such may also at least partially control or regulate the activation, deactivation, power up, sleep mode, etc. of the control circuitry 40 as well as the display device 45 itself. In use, the display device 45 will provide a visual indication for operating personnel of the pressure values or pressure readings of the retaining cuff 100 through operation of the sensor module 44 being disposed in fluid communication with the pressure chamber 14 and by virtue of the attachment of the outlet lumen 32, to the common pressure maintained within the retaining cuff 100. As also noted in the embodiment of FIG. 2, the display device 45 may include an alarm or information indicator in the form of an LED 47. The indicator 47 will serve to alert a user or operator of the operative characteristics or conditions of the assembly 10 including, but not limited to, excessive pressure within the retaining cuff 100, power conditions of the self-contained power source or battery 42, and other pre-determined or preferred conditions associated with the intended and proper functioning of the assembly 10. Such other operative conditions may include power-off and power-on modes of the control circuitry 40 and/or display device 45 as well as other operative components of the inflating and monitoring assembly 10 of the present invention.

To further conserve energy of the self-contained power source, the control circuitry and microprocessor 40 may also be structured to normally assume the "sleep mode" subsequent to it being first activated for use during a monitoring session, as set forth above. Therefore, cooperative structuring between the display device 45 and control circuitry 40 facilitates the powering-up of the control circuitry 40 upon a selective activation of the display device 45. Such selective activation may be accomplished by utilizing or affecting the aforementioned a touch activation of the display device 45. Therefore, when not performing a monitoring, reading or display function of the pressure readings of the retaining cuff 100, at least the microprocessor of the control circuitry 40 and the pressure sensor 44 normally assume a sleep mode. Due to this cooperative structuring between the display device 45 and the control circuitry 40 a touch activation of the display device 45 will result in full activation of the display device 45 concurrent to activation of the microprocessor of the control circuitry 40 from their respective sleep modes into their respective power-up modes. However, it is noted that in at least one preferred embodiment the pressure sensor 44 will remain in a sleep mode unless actual pressure monitoring is being conducted. This is due to the fact that the pressure sensor or pressure module 44 consumes relatively large amounts of power.

Other operative features associated with one or more preferred embodiments of the inflating and monitoring assembly 10 include the control circuitry and microprocessor 40 as well as the pressure sensor or sensor module 44 cooperatively structured to include "multilevel sampling capabilities". The "multilevel sampling capabilities" are also directly associated with the conservation of power in order to extend the operable life of the self-contained power source 42. Accordingly, the control circuitry and microprocessor 40 are operatively structured with the pressure sensor or sensor module 44 to effectively accomplish power modulation to the pressure sensor or sensor module 44, during the multilevel sampling procedure. More specifically, the multilevel sampling capabilities comprise a sampling or monitoring of the pressure of the retaining cuff 100 at different rates or frequencies. Therefore, the multilevel sampling capabilities include at least a high rate sampling mode and a low rate sampling mode. Further, the high rate sampling mode includes a sampling frequency sufficient to determine substantially real-time pressure values of the retaining cuff and may occur at multiple times per second such as, but not limited to, 4 times per second. In contrast, the low rate sampling mode comprises a sampling frequency of generally about once every 1-2 seconds. Therefore, power to and consumed by the pressure sensor or sensor module 44 varies, so as to conserve energy of the self-contained power source or battery 42 associated with the monitoring assembly 10. As such, during the high rate sampling mode, the pressure sensor 44 will be maintained in the "sensor power mode" a sufficient amount of time to obtain pressure readings at the higher sampling rate. Therefore, more power will be consumed by the pressure sensor 44 during this high rate sampling mode. In contrast, the pressure sensor 44 will be allowed to assume the "sleep mode" and thereby consume less energy during the low rate sampling mode, when the common pressure within the pressure chamber 14 and retaining cuff 100 is not actually being monitored or determined. This is due, as set forth above, to the fact that the sensor module may be activated only about once every 1-2 seconds, rather than multiple times per second as is the case during the high rate sampling mode. It is therefore again emphasized that the variation in sampling rates, as well as the overall capability of placing the microprocessor of the control circuitry 40 and the pressure sensor 44 in either the "sleep mode" or "sensor power mode" serves to effectively save energy delivered by the self-contained power source 42.

In addition, the multilevel sampling capabilities include "dynamic operating characteristics" comprising automatic changes of sampling rates or frequencies, dependent at least in part, on a "time basis" as well as the pressure stability of the retaining cuff 100. Accordingly, when the pressure within the retaining cuff 100 remains substantially stable over a predetermined period of time, for example 2 minutes, the dynamic operating characteristics of the multilevel sampling capabilities will automatically change the frequency of pressure sampling or reading from the high rate sampling mode to the low rate sampling mode. In addition, the sampling rate or sampling frequency will automatically be changed back from the low rate sampling mode to the high rate sampling mode upon an a determination of an actual change in the pressure of the retaining cuff 100 or the occurrence of one or more predetermined external events, which may be interpreted by the control circuitry as an attempt to disconnect the fluid communicating connection 30.

The occurrence of a predetermined external event may also cause the dynamic operating capabilities to automatically change the sampling rate or frequency from the low rate sampling mode to the high rate sampling mode, when any event occurs which would appear to or be interpreted by the microprocessor and control circuitry 40 to affect the pressure within the retaining cuff 100. By way of example only, an intended manual adjustment or an inadvertent contact or manipulation of the outlet lumen 32, such as by a dislodgement thereof relative to the outlet 18, may be interpreted by the microprocessor and control circuitry 40 as an attempt to remove the retaining cuff 100 from its intended fluid communication with the pressure chamber 14. In order to assure a substantially real-time evaluation and monitoring of the pressure within the retaining cuff 100, during such an external event, the high rate sampling mode will be established in order to accurately determine the pressure of the retaining cuff 100 on a substantially real-time basis. However the external event, as set forth above, may be inadvertent and misinterpreted by the control circuitry 40 and in fact not be an attempted reduction of the pressure within the retaining cuff 100.

As additionally set forth herein, the monitoring assembly 10 of the present invention is powered by a self-contained battery source 42. It is also noted that the power requirements of the pressure sensor 44 is significantly greater, in orders of magnitude higher, than other components operatively associated with the control circuitry 40. In order to save battery life and reduce power output, the power to the pressure sensor 44 may be modulated or supplied on a periodic basis rather than continuously. As a result, the pressure sensor 44 at least partially controlled by the microprocessor and control circuitry 40 may be disposed in either the "sleep mode" or the "sensor power mode", as indicated. Therefore, the microprocessor and control circuitry further comprises "periodic sampling capabilities" which in turn may be accomplished by "power pulsing" of the pressure sensor 44. As such, the power pulsing procedure may include periodic power-on activation into the "sensor power mode" and a subsequent power-off deactivation of the pressure sensor 44 into the "sleep mode". Therefore, the pressure sensor 44 is structured to monitor pressure of the retaining cuff 100 on a periodic basis, during the power-on activation thereof. Further, the control circuitry and microprocessor 40 are structured to instigate the aforementioned power-off deactivation, subsequent to the monitoring of pressure of the retaining cuff 100 by the pressure sensor 44. As a result power drain from the battery 42 will be minimized, and the battery life will be extended.

It should be further noted that the aforementioned and described multilevel sampling capabilities may be implemented, at least in part, with the aforementioned power pulsing capabilities. However, in at least one preferred embodiment the periodic sampling capabilities may operatively replace the aforementioned multilevel sampling capabilities. Such independent operation, exclusively under the "power pulsing" procedure, is operative to include the periodic power-on activation and subsequent power-off deactivation in a manner which is independent of the multilevel sampling of pressure within the retaining cuff 100 at different rates or frequencies, as indicated. Accordingly, in order to maintain or extend the operable life of the self-contained battery source 42, power is only directed to the pressure sensor 44 when it is time to read or monitor the pressure within the retaining cuff 100. Thereafter, current to the pressure sensor 44 is turned off at all other times. Further, in at least one preferred embodiment, the pressure sensor 44 may require a predetermined period of time such as, by way of example only, 20 milliseconds to stabilize its pressure reading after power-on activation has been accomplished. More specifically, each time power is pulsed to the pressure sensor 44, to read the pressure within the retaining cuff 100, the power-on activation of the pressure sensor 44 will be maintained for at least the predetermined time period of, by way of example only, 20 mS. The output from the pressure sensor 44 is then read or determined during this period of time and the current to the pressure sensor 44 is immediately turned off, resulting in the aforementioned power-off deactivation thereof. This cycle constitutes one sampling cycle.

Yet additional structural and operative features of the system and the inflating and monitoring 10 include the control circuitry 40 comprising a sufficient memory and/or memory capabilities to store intended or required calibration parameters. Such calibration parameters may typically include, but not be limited to, the establishment and monitoring of an appropriate pressure within the retaining cuff 100. Therefore, the calibration parameters will be dependent on utilization of the system and assembly, the length of intended monitoring session, cooperative structuring and operation of the various components and features of the system and assembly 10, etc. However all of the aforementioned calibration parameters needed for accurate operation, in terms of determination and display of pressure readings, will be downloaded prior to a first use or first activation of the assembly and during the structuring, formation, assembly, etc. of the assembly 10. More specifically, when the monitoring assembly 10 is being formed, structured and assembled and prior to its initial use or activation, all of the calibration parameters and data are downloaded into the memory of the control circuitry 40.

Further, the memory is structured to store and maintain the downloaded calibration parameters, while the control circuitry is in a power-off mode, such as prior to its first use or activation for its first monitoring session. Therefore, upon an initial or first activation of the control circuitry 40, when the monitoring assembly 10 is ready for use, the calibration parameters relating to pressure monitoring, etc. will be implemented. As a result, there is no need to calibrate the control circuitry and/or other operative components of the inflating and monitoring assembly 10 after it has been initially activated for its first use in a monitoring session.

Additional features of one or more preferred embodiments of the system and assembly 10 include "limited use capabilities" comprising structuring the control circuitry 40 for permanent deactivation after one or more uses and or monitoring sessions. More specifically, the limited use capabilities may comprise operative features which allow the monitoring assembly 10 to be a single use device or alternatively capable of being used for a limited or predetermined number of monitoring sessions. In accordance therewith, the switching assembly 46 including the switch member 48, is structured and operative to deactivate the control circuitry 40 upon the removal of the outlet lumen 32 from the fluid communicating connection 30 or outlet 18. The switching assembly 46 may also be structured to activate the control circuitry 40 upon the introduction or establishment or insertion of the outlet lumen 32 into the outlet 18 so as to establish, connect or define the fluid communicating connection 30. This initial activation of the control circuitry 40 may occur when the retaining cuff 100 is first connected in fluid communication with the interior of the pressure chamber 14 by virtue of the attachment of the outlet lumen 32 to the outlet 18. As set forth above, the control circuitry 40 may normally or initially be disposed in a sleep mode and will be automatically activated upon establishment of the fluid communicating connection 30 of the retaining cuff 100 with the pressure chamber 14. This in turn is caused by the insertion of the outlet lumen 32 into the outlet 18.

As set forth herein, the control circuitry 40 of the inflating and monitoring assembly 10, include the aforementioned limited use capabilities. Accordingly, the removal of the outlet lumen 32 and the disconnection of the fluid communicating connection 30 may activate the single use or limited use capabilities. However, in order to come to overcome any inadvertent manipulation, handling, or other external event which would be perceived or interpreted by the control circuitry 40 as an attempt to disconnect the fluid communicating connection 30, the control circuitry 40 includes a "time delay facility". The time delay facility is operatively connected to the control circuitry 40 and is structured to delay permanent deactivation of the control circuitry 40 for a predetermined period of time. As a result any inadvertent contact or intentional manipulation of the fluid communicating connection 30 such as by contact with the outlet lumen 32 adjacent the outlet 18, which could be interpreted by the control circuitry as an attempt to disconnect the fluid communicating connection 30 will not, at least for a period of time, result in the permanent deactivation of the control circuitry 40. As noted, such predetermined time period associated with the time delay facility may be as little as a few seconds or as long as one or two minutes, before the remainder of the monitoring assembly 10 is rendered inoperable and incapable of further or repeated use. It is noted that the length of the time delay should be such as to allow a user to reconnect the fluid communicating connection 30 or make any other adjustments which will prevent the inflating and monitoring assembly 10 from further use.

Yet additional structural and operative features of both the modular and integrated embodiments as set forth above include memory capabilities Incorporated within the control circuitry 40 which serves to store data resulting from the monitoring of pressure within the retaining cuff 100. In addition, the monitoring data could be saved to the memory capabilities of the control circuitry 40 and be later downloaded to a patient's electronic medical records storage, healthcare personnel or other healthcare facilities databases. Accordingly, the system and monitoring assembly of the present invention could include structure which facilitates hardwire or wireless transmission of the stored data from the memory capabilities to the appropriate location, as preferred or required. Such stored data of the monitoring procedures in any given monitoring session allows clinicians to analyze data, provide records for insurers and/or demonstrate that the healthcare facility is following proper procedures for preventing tracheal trauma, by keeping pressures of the retaining cuff 100 within the appropriate and/or predetermined safe ranges. By way of example, monitoring data should be recorded upon the clinician monitoring cuff pressure every 6 hours and/or during a shift change. The ability to store the monitoring data provides significantly greater data points and provides a "watchdog" for insurance company to ensure that clinicians are actually monitoring pressure for supporting malpractice lawsuit defense. This may also provide incentive for the clinicians to be more diligent in their cuff monitoring procedures.

In addition to the above, the control circuitry 40 and additional associated operative components working in cooperation there with could accomplish wireless transmissions. More specifically, a wireless or other appropriate communication facilities could be incorporated in the control circuitry 40, as set forth above, for the purpose of transmitting notifications to clinicians when the pressure data and/or intended or predetermined parameters were not within a preset acceptable range. Such data could be wirelessly uploaded to a secure database for maintaining accurate records of procedures and during the one or more sampling sessions with which the system and monitoring assembly 10 of the present invention is associated or utilized.

Somewhat similar to the above noted wireless and/or mobile communication facilities associated with the monitoring assembly 10 and the included monitoring system, will be appropriate computer applications or software that allows the monitoring data and or the monitoring procedure itself to be managed and edited, utilizing a mobile communication device such as a smart phone, laptop, etc.

As set forth above, and with specific reference to FIG. 1 the monitoring assembly 10 of the present invention can be utilized and made available in either a modular construction embodiment as at least generally described in FIGS. 4 and 5 or an integrated construction embodiment. In the latter structural configuration, the monitoring assembly 10, including the housing 12 comprises the inlet and outlet 16 and 18 respectively being fixedly interconnected to the fluid pressure source 22 and to the retaining cuff 100. Fixed or permanent connection of the outlet 18 to the retaining cuff 100 may be accomplished by an interconnecting outlet lumen 32. Moreover, the fluid pressure source 22 can be fixedly connected to the inlet 16 either directly, as generally represented in FIG. 4. As such, the nozzle 20 and the inlet 16 are cooperatively structured to accomplish the aforementioned fixed connection, rather than being removable attached. In the alternative, and or inlet lumen 52 may serve to fixedly and permanently interconnect the fluid pressure source 22 to the housing 12 and the outlet 16.

Accordingly, the integrated construction, as versus the modular construction, at least partially comprises the housing 12, the control circuitry 40 and at least the retaining cuff 100 being fixedly and/or permanently attached at least to the extent of being made available and utilized together in a generally "kit format". In addition, the integrated construction may also include the fluid pressure source 22 being fixedly connected to the housing 12 by virtue of the direct connection with the inlet 16 or by a fixed interconnection therewith via the inlet or inflation lumen 52.

It is emphasized that many of the structural and operative features of the monitoring assembly 10, whether in its modular format or integrated format, as explained above, are the same. As such, the monitoring assembly 10, whether in the modular construction or the integrated construction, may include multilevel sampling capabilities including dynamic operating characteristics comprising automatic changes of sampling rates or frequencies as explained. In combination therewith or in addition, the control circuitry 40 may be structured to include periodic sampling capabilities comprising power pulsing of the pressure sensor 44 including the aforementioned and described periodic power-on activation and subsequent power-off deactivation which defines a single sampling cycle.

In addition, both the modular and integrated embodiments of the monitoring assembly 10 may include the memory capabilities including calibration parameters stored therein prior to a first activation of the control circuitry 40. As such the control circuitry 40 and the memory capabilities associated therewith are structured and operative to maintain the calibration data in a stored state during an initial power-off condition, prior to the first activation of the control circuitry 40.

However, at least one structural and operational distinction between the modular embodiment and the integrated construction of the monitoring assembly 10 includes the absence of the trigger or switch mechanism 48 as described with primary reference to FIGS. 4 and 5 of the modular embodiment. More specifically, the control circuitry 40 of the integrated construction embodiment comprises activating facilities structured to activate the control circuitry upon a detection of a "fluid variance" within the pressure chamber 14. In more specific terms, the activation facilities associated with the control circuitry 40 comprises a fluid flow detector which may be mounted in direct fluid communication with or within the pressure chamber 14. The fluid flow detector and/or and associated part of the control circuitry 40 is structured to determine fluid movement and or the passage of air or other inflating gas within and or through the pressure chamber 14. In addition, the pressure variance may also comprise a pressure increase within the pressure chamber 14, such as when inflating, pressurizing fluid is first introduced into the pressure chamber 14 from the fluid pressure source 22 via the inlet lumen 52. It is further noted that initial activation or "turn-on" of the monitoring assembly 10 may be accomplished by a simple manually activated button and/or icon 49 present on the display 45.

In somewhat similar terms of operation, the pressure sensor 44 may be operatively connected to the activation facilities and structured to determine a pressure increase and/or a pressure decrease. As such, the pressure sensor 44 is structured to assume an on-off low power sampling mode operative to periodically sample for a predetermined pressure increase within the pressure chamber 44 as generally indicated above. Operatively associated therewith, the control circuitry 40 is further structured to include deactivation facilities structured to deactivate the control circuitry 40 upon at least a fluid variance within the pressure chamber as generally indicated. In this instance deactivation of the monitoring assembly 10 and control circuitry 40 will be accomplished if the pressure variance within the pressure chamber 14 is significantly decreased, even to the point of reaching ambient pressure. Such a significant decrease may occur, but is not limited to, the occurrence of a detachment of the outlet lumen 32 from the retaining cuff 100 and or the monitoring assembly 10. In each of the above noted situations involving the determination of "pressure variance" within the pressure chamber 14, the determination of fluid movement or fluid flow therein and or a decrease in existing pressure must last for a predetermined duration of time.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A system operative to monitor pressure within a retaining cuff generated by a pressurized fluid flow, said system comprising:
    a retaining cuff,
    a housing including a chamber housing and a pressure chamber, said pressure chamber having an inlet and an outlet, said retaining cuff integrally interconnected to said outlet, said pressure chamber disposed on an inside of said chamber housing,
    said inlet structured for connection to a fluid pressure source and said outlet comprising a fluid communicating connection with said pressure chamber,
    control circuitry connected to said housing and structured to regulate operation of a pressure sensor; said pressure sensor disposed in fluid communication with said pressure chamber and said retaining cuff; said pressure sensor at least partially disposed on said inside of said chamber housing,
    said fluid communicating connection structured to concurrently establish a substantially common pressure in said pressure chamber and said retaining cuff, said pressure sensor structured to determine said substantially common pressure,
    said inlet configured to permit passage there through of a pressurized fluid flow from the fluid pressure source to said pressure chamber, said outlet configured to permit passage there through of the pressurized fluid flow out of said pressure chamber,
    a switching assembly mounted on said housing, said switching assembly comprising a switch disposed in adjacent relation to said outlet, said switch structured to respectively deactivate and activate said control circuitry upon a disconnect and connect of a fluid connecting conduit, and
    said pressure sensor and said control circuitry cooperatively structured to sample said retaining cuff at different rates, said control circuitry structured to change said sampling rate to an optimal sampling rate based upon said substantially common pressure determined by said pressure sensor over a predetermined period of time.

2. The system as recited in claim 1 further comprising the fluid pressure source fixedly connected in fluid communication with said inlet.

3. The system as recited in claim 1 wherein each of said control circuitry is structured to reduce a sampling rate of said pressure sensor and reduce power consumption thereby upon said substantially common pressure remaining uniform for said predetermined period of time.

4. The system as recited in claim 3 wherein said control circuitry is structured to increase a sampling rate of said pressure sensor in the event of fluctuations in said substantially common pressure identified by said pressure sensor.

5. The system as recited in claim 4 wherein said control circuitry is structured to switch said pressure sensor between at least a high rate sampling mode and a low rate sampling mode; said high rate sampling mode including a sampling frequency sufficient to determine real-time pressure readings of the retaining cuff.

6. The system as recited in claim 1 wherein said control circuitry further comprises periodic sampling capabilities comprising power pulsing of said pressure sensor including periodic power-on activation and power-off deactivation of said pressure sensor.

7. The system as recited in claim 6 wherein said pressure sensor is structured to monitor said substantially common pressure of said pressure chamber and said retaining cuff during said periodic power-on activation, said control circuitry further structured to instigate said power-off deactivation subsequent to the monitoring of said substantially common pressure by said pressure sensor during said power-on activation thereof.

8. The system as recited in claim 1 wherein said control circuitry comprises memory capabilities including calibration parameters stored therein prior to a first activation of said control circuitry; said control circuitry and said memory capabilities being further structured to maintain said calibration data in a stored state during a no-powered mode prior to the first activation of said control circuitry; said control circuitry further structured to activate and implement said calibration parameters upon the first activation of said control circuitry.

9. The system as recited in claim 8 wherein said control circuitry comprises activating facilities structured to activate said control circuitry upon a detection of a fluid variance within said pressure chamber.

10. The system as recited in claim 9 wherein said activation facilities comprise a fluid flow detector disposed in fluid communication with said pressure chamber and structured to determine fluid movement within said pressure chamber; said fluid variance comprising said fluid movement within said pressure chamber.

11. The system as recited in claim 9 wherein said fluid variance comprises a predetermined pressure increase within said pressure chamber.

12. The system as recited in claim 11 wherein said pressure sensor is operatively connected to said activation facilities and structured to determine said pressure increase.

13. The system as recited in claim 12 wherein said pressure sensor is structured to assume an on-off low power sampling mode operative to periodically sample for said predetermine pressure increase within said pressure chamber.

14. The system as recited in claim 1 wherein said control circuitry further comprises deactivation facilities structured to deactivate said control circuitry upon at least a fluid variance within said pressure chamber.

15. The system as recited in claim 14 wherein said fluid variance comprises a predetermined pressure decrease within said pressure chamber.

16. The system as recited in claim 15 wherein said fluid variance further comprises said predetermined pressure decrease existing over a predetermined duration.

17. The system as recited in claim 15 wherein said predetermined pressure decrease comprises a decrease to substantially ambient pressure.

18. The system as recited in claim 1 wherein said outlet is configured to permit passage there through the pressurized fluid flow out of said pressure chamber and into a fluid connecting conduit.

\* \* \* \* \*